(12) United States Patent
Fergione et al.

(10) Patent No.: US 7,790,197 B2
(45) Date of Patent: Sep. 7, 2010

(54) PHARMACEUTICAL COMPOSITIONS OF ATORVASTATIN

(75) Inventors: Michael B. Fergione, Stonington, CT (US); Barbara A. Johnson, Niantic, CT (US); Kenneth Craig Waterman, Waterford, CT (US)

(73) Assignee: Warner-Lambert Company LLC, Ann Arbor, MI (US)

( * ) Notice: Subject to any disclaimer, the term of this patent is extended or adjusted under 35 U.S.C. 154(b) by 542 days.

(21) Appl. No.: 10/828,079

(22) Filed: Apr. 20, 2004

(65) Prior Publication Data

US 2004/0247673 A1 Dec. 9, 2004

Related U.S. Application Data

(60) Provisional application No. 60/478,119, filed on Jun. 12, 2003.

(51) Int. Cl.
A61K 9/26 (2006.01)
(52) U.S. Cl. .................. 424/470; 424/489; 424/494; 424/480
(58) Field of Classification Search .................. None
See application file for complete search history.

(56) References Cited

U.S. PATENT DOCUMENTS

| | | |
|---|---|---|
| 4,681,893 A | 7/1987 | Roth |
| 5,003,080 A | 3/1991 | Butler et al. |
| 5,097,045 A | 3/1992 | Butler et al. |
| 5,103,024 A | 4/1992 | Millar et al. |
| 5,124,482 A | 6/1992 | Butler et al. |
| 5,149,837 A | 9/1992 | Butler et al. |
| 5,155,251 A | 10/1992 | Butler et al. |
| 5,216,174 A | 6/1993 | Butler et al. |
| 5,245,047 A | 9/1993 | Butler et al. |
| 5,248,793 A | 9/1993 | Millar et al. |
| 5,273,995 A | 12/1993 | Roth |
| 5,280,126 A | 1/1994 | Butler et al. |
| 5,298,627 A | 3/1994 | Butler et al. |
| 5,342,952 A | 8/1994 | Butler et al. |
| 5,397,792 A | 3/1995 | Butler et al. |
| 5,446,054 A | 8/1995 | Butler et al. |
| 5,470,981 A | 11/1995 | Butler et al. |
| 5,489,690 A | 2/1996 | Butler et al. |
| 5,489,691 A | 2/1996 | Butler et al. |
| 5,510,488 A | 4/1996 | Butler et al. |
| 5,686,104 A | 11/1997 | Mills et al. |
| 5,969,156 A | 10/1999 | Briggs et al. |
| 5,998,633 A | 12/1999 | Jacks et al. |
| 6,087,511 A | 7/2000 | Lin et al. |
| 6,121,461 A | 9/2000 | McKenzie |
| 6,126,971 A | 10/2000 | Mills et al. |
| 6,242,003 B1 | 6/2001 | Kalb et al. |
| 6,274,740 B1 | 8/2001 | Lin et al. |
| 6,395,300 B1 | 5/2002 | Straub et al. |
| 6,433,213 B1 | 8/2002 | Bosch et al. |
| 6,476,235 B2 | 11/2002 | Butler et al. |
| 6,605,729 B1 | 8/2003 | Byrn et al. |

FOREIGN PATENT DOCUMENTS

| | | |
|---|---|---|
| EP | 0 848 705 B1 | 2/1997 |
| EP | 1 027 886 A2 | 8/2000 |
| EP | 1 226 818 A | 7/2002 |
| WO | WO 94/16693 A | 8/1994 |
| WO | WO 00/71116 A1 | 11/2000 |
| WO | WO 00/72825 A1 | 12/2000 |
| WO | WO 01/28999 A1 | 4/2001 |
| WO | WO 01/36384 A1 | 5/2001 |
| WO | WO 01/42209 A1 | 6/2001 |
| WO | WO 01/74394 | 10/2001 |
| WO | WO 01/76566 | * 10/2001 |
| WO | WO 01/76566 A | 10/2001 |
| WO | WO 02/41834 A2 | 5/2002 |
| WO | WO 02/43667 A2 | 6/2002 |
| WO | WO 02/43732 A1 | 6/2002 |
| WO | WO 02/051084 A1 | 7/2002 |
| WO | WO 02/051385 A1 | 7/2002 |

(Continued)

OTHER PUBLICATIONS

Takemoto, M., et al, "Statins as antioxidant therapy for preventing cardiac myocyte hypertrophy", The Journal of Clinical Investigation, Nov. 2001, vol. 108, No. 10, pp. 1429-1437.
Konno, T., Chem. Pharm. Bull., 1990, vol. 38, pp. 2003-2007.
U.S. Appl. No. 10/828,419.
U.S. Appl. No. 10/828,398.
U.S. Appl. No. 10/828,488.
PCT Search Report, PCT/IB2004/001862.

Primary Examiner—Robert A Wax
Assistant Examiner—Hasan S Ahmed
(74) Attorney, Agent, or Firm—Jennifer A. Kispert; J. Michael Dixon

(57) ABSTRACT

A wet granulated pharmaceutical composition comprising atorvastatin or a pharmaceutically acceptable salt thereof with less than about 5 weight % of an alkaline earth metal salt additive with a disintegrant which provides the atorvastatin with not more than about 3% atorvastatin lactone based on the ratio of lactone peak area compared to the total drug-related peak integrated areas, as well as said wet granulated pharmaceutical composition comprising atorvastatin or a pharmaceutically acceptable salt thereof in combination with at least one other active drug, methods for preparing said compositions, kits for containing such compositions, and a method of treating hypercholesterolemia and/or hyperlipidemia, osteoporosis, benign prostatic hyperplasia (BPH), and Alzheimer's disease using a therapeutically effective amount of the pharmaceutical compositions.

4 Claims, No Drawings

FOREIGN PATENT DOCUMENTS

| | | |
|---|---|---|
| WO | WO 02/057228 A1 | 7/2002 |
| WO | WO 02/057229 A1 | 7/2002 |
| WO | WO 02/057274 A1 | 7/2002 |
| WO | WO 02/059087 A1 | 8/2002 |
| WO | WO 02/062824 A2 | 8/2002 |
| WO | WO 02/072073 * | 9/2002 |
| WO | WO 02/072073 A | 9/2002 |
| WO | WO 02/083637 A1 | 10/2002 |
| WO | WO 02/089788 | 11/2002 |
| WO | WO 03/018547 A2 | 3/2003 |
| WO | WO 03/039542 | 5/2003 |
| WO | WO 03/068191 | 8/2003 |
| WO | WO 2004/022053 | 3/2004 |

\* cited by examiner

PHARMACEUTICAL COMPOSITIONS OF ATORVASTATIN

CROSS-REFERENCE TO RELATED APPLICATIONS

This application claims priority from U.S. Provisional Patent Application No. 60/478,119 filed Jun. 12, 2003.

FIELD OF THE INVENTION

This invention relates to pharmaceutical compositions comprising atorvastatin and pharmaceutically acceptable salts thereof and a process for the preparation of the same, kits containing such compositions, as well as methods of using such compositions to treat subjects suffering from hypercholesterolemia and/or hyperlipidemia, as well as osteoporosis, benign prostatic hyperplasia (BPH), and Alzheimer's disease.

BACKGROUND OF THE INVENTION

The conversion of 3-hydroxy-3-methylglutaryl-coenzyme A (HMG-CoA) to mevalonate is an early and rate-limiting step in the cholesterol biosynthetic pathway. This step is catalyzed by the enzyme HMG-CoA reductase. Statins inhibit HMG-CoA reductase from catalyzing this conversion. As such, statins are collectively potent lipid lowering agents.

Atorvastatin calcium, disclosed in U.S. Pat. No. 5,273,995 which is incorporated herein by reference, is currently sold as Lipitor® having the chemical name [R—(R*,R*)]-2-(4-fluorophenyl)-β,δ-dihydroxy-5-(1-methylethyl)-3-phenyl-4-[(phenylamino)carbonyl]-1H-pyrrole-1-heptanoic acid calcium salt (2:1) trihydrate and the formula

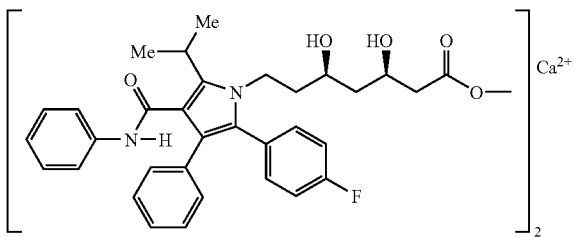

Atorvastatin and pharmaceutically acceptable salts thereof are selective, competitive inhibitors of HMG-CoA reductase. As such, atorvastatin calcium is a potent lipid-lowering compound and is thus useful as a hypolipidemic and/or hypocholesterolemic agent, as well as in the treatment of osteoporosis, benign prostatic hyperplasia (BPH), and Alzheimer's disease.

A number of patents have issued disclosing atorvastatin, formulations of atorvastatin, as well as processes and key intermediates for preparing atorvastatin. These include: U.S. Pat. Nos. 4,681,893; 5,273,995; 5,003,080, 5,097,045; 5,103,024; 5,124,482; 5,149,837; 5,155,251; 5,216,174; 5,245,047; 5,248,793; 5,280,126; 5,397,792; 5,342,952; 5,298,627; 5,446,054; 5,470,981; 5,489,690; 5,489,691; 5,510,488; 5,686,104; 5,998,633; 6,087,511; 6,126,971; 6,433,213; and 6,476,235, which are herein incorporated by reference.

Atorvastatin can exist in crystalline, liquid crystalline and non-crystalline and amorphous forms.

Crystalline forms of atorvastatin calcium are disclosed in U.S. Pat. Nos. 5,969,156 and 6,121,461, which are herein incorporated by reference. Further crystalline forms of atorvastatin are disclosed U.S. Pat. No. 6,605,729 which is herein incorporated by reference.

Additionally, a number of published International Patent Applications have disclosed crystalline forms of atorvastatin, as well as processes for preparing amorphous atorvastatin. These include: WO 00/71116; WO 01/28999; WO 01/36384; WO 01/42209; WO 02/41834; WO 02/43667; WO 02/43732; WO 02/051804; WO 02/057228; WO 02/057229; WO 02/057274; WO 02/059087; WO 02/083637; WO 02/083638; WO 03/011826; WO 03/050085; WO 03/070702; and WO 04/022053.

It has been disclosed that the amorphous forms in a number of drugs exhibit different dissolution characteristics and in some cases different bioavailability patterns compared to the crystalline form (Konno, T., Chem. Pharm. Bull., 1990; 38:2003-2007). For some therapeutic indications one bioavailability pattern may be favored over another.

Variations in dissolution rates can make it advantageous to produce atorvastatin formulations in either crystalline or amorphous forms. For example, for some potential uses of atorvastatin (e.g., acute treatment of patients having strokes as described in Takemoto, M.; Node, K.; Nakagami, H.; Liao, Y.; Grimm, M.; Takemoto, Y.; Kitakaze, M.; Liao, J. K., Journal of Clinical Investigation, 2001; 108(10): 1429-1437) a rapid onset of activity may be highly beneficial in improving the efficacy of the drug.

The preparation of solid formulations of atorvastatin is described in U.S. Pat. Nos. 5,686,104 and 6,126,971. In the process described therein, atorvastatin is combined with a stabilizing additive, such as, an alkaline earth metal salt, and excipients and subjected to wet granulation using a combination of water and a surfactant (Tween™ 80). Because alkaline earth metal salt additives can affect atorvastatin bioavailability, there remains a need to provide atorvastatin in a wet granulated composition wherein said composition is substantially free of an alkaline earth metal salt additive. Similarly, it can be desirable to minimize the use of any alkalizing agent additives in a composition of atorvastatin to avoid potential bioavailability issues and avoid interactions when the drug is used in combination dosage forms with other drugs.

Concurrently filed United States Patent Applications, commonly owned, Ser. No. 10/828,419 discloses a unit dosage form comprising atorvastatin or a pharmaceutically acceptable salt thereof prepared without a granulation step and Ser. No. 10/828,398 discloses a dry-granulated pharmaceutical composition comprising atorvastatin or a pharmaceutically acceptable salt thereof.

In preparation and storage of dosage forms of atorvastatin, it is important to provide the active drug in a pure form. Moreover, it is desirable to achieve this high purity and stability with as simple a formulation as possible. There remains a need to provide simple formulations and processes for preparation of unit dosage forms of atorvastatin that have low levels of impurities. Moreover, there remains a need to provide atorvastatin formulations suitable for unit dosage forms whereby adequate drug purity, stability, and desired dissolution rate and bioavailability is provided with minimal addition of alkalizing agents.

One preferred unit dosage form for atorvastatin is a tablet. For active drugs in tablets to be rapidly absorbed once swallowed, it is generally important for the tablet to disintegrate rapidly once exposed to fluids in the gastrointestinal tract. At the same time, it is important that the tablets be sufficiently hard that they do not fracture or chip during manufacturing, handling or storage. These seemingly contradictory needs can be met by addition of disintegrants to the composition. A number of disintegrants for compositions of atorvastatin have been disclosed in the prior art including calcium carboxymethylcellulose, starch and croscarmellose sodium (see U.S.

Pat. Nos. 5,686,014 and 6,126,971). When using atorvastatin with minimal levels of an alkalizing additive or an alkaline earth metal salt additive, we have unexpectedly found that with the standard wet granulation process, only certain disintegrants provide for tablets of atorvastatin with acceptable purity. This is especially unexpected since the disintegrant used in commercial formulations (croscarmellose sodium) was found to be unacceptable for wet granulations of amorphous atorvastatin with minimal levels of added alkalizing additives or alkaline earth metal salt additives. Moreover, this stability is unexpectedly maintained even when the atorvastatin is in an amorphous form. In addition to formulation improvements, we have developed wet granulation processes for incorporation of disintegrants into formulations that provide atorvastatin with high purity, even for disintegrants that provide poor stability with the standard process.

We have further found that when using a wet granulation of atorvastatin (especially non-crystalline atorvastatin), purity of the drug can be improved by addition of volatile bases to the granulation solvent. These volatile bases provide for improved purity of the drug in the dosage form, yet are not themselves present in the final dosage form, and as such cannot affect the bioavailability.

Therefore, it is an object of the present invention to provide a stable dosage form of atorvastatin having a good disintegration rate and bioavailability. It is a further object of the present invention to provide a stable and pure composition of atorvastatin with minimal levels of alkaline earth metal salt additives or other added alkalizing agents in the composition.

SUMMARY OF THE INVENTION

Accordingly, the first aspect of the present invention is a wet granulated pharmaceutical composition of atorvastatin with less than about 5 weight % of an alkaline earth metal salt additive comprising:
(a) atorvastatin or a pharmaceutically acceptable salt thereof; and
(b) a disintegrant or combination of disintegrants, wherein said wet granulated pharmaceutical composition contains not more than about 3% atorvastatin lactone based on the ratio of lactone peak area compared to the total drug-related peak integrated areas using HPLC.

A second aspect of the present invention is a wet granulated pharmaceutical composition of atorvastatin with less than about 5 weight % of an alkaline earth metal salt additive comprising:
(a) atorvastatin or a pharmaceutically acceptable salt thereof in combination with at least one active drug; and
(b) a disintegrant or combination of disintegrants, wherein said wet granulated pharmaceutical composition contains not more than about 3% atorvastatin lactone based on the ratio of lactone peak area compared to the total drug-related peak integrated areas using HPLC.

A third aspect of the present invention is a method for preparing a wet-granulated composition of atorvastatin comprising:
(a) combining atorvastatin or a pharmaceutically acceptable salt thereof with sodium starch glycolate, starch, sodium alginate, powdered cellulose, hydroxypropylcellulose, magnesium aluminum silicate or polacrilin potassium or combinations thereof, and optionally other excipients;
(b) adding sufficient water, isopropanol, ethanol, or a mixture thereof to the atorvastatin blend from step (a) under shear to generate granules;
(c) optionally milling or sieving said wet granules;
(d) drying said granules;
(e) optionally milling, grinding or sieving said granules;
(f) optionally mixing in other excipients; and
(g) optionally, forming the composition into unit dosage forms.

A fourth aspect of the present invention is a method for preparing a wet granulated composition of atorvastatin comprising:
(a) combining atorvastatin or a pharmaceutically salt thereof with a diluent with less than 2 weight % of a disintegrant;
(b) adding sufficient water, isopropanol, ethanol, or a mixture thereof to the atorvastatin blend from step (a) under shear to generate granules;
(c) optionally milling, grinding or sieving said wet granules;
(d) drying said granules;
(e) optionally milling, grinding or sieving said granules;
(f) mixing in a disintegrant and optionally other excipients; and
(g) optionally, forming the composition into unit dosage forms.

A fifth aspect of the present invention is a method for preparing a wet granulated composition of atorvastatin comprising:
(a) combining atorvastatin or a pharmaceutically acceptable salt thereof and one or more excipients;
(b) adding, under shear, a sufficient amount of a solution of a volatile base dissolved in water, isopropanol or ethanol or a mixture thereof, to generate granules;
(c) optionally milling, grinding or sieving said wet granules;
(d) drying said granules;
(e) optionally milling, grinding or sieving said granules;
(f) optionally mixing in other excipients as needed to make the final composition; and
(g) optionally, forming said composition into unit dosage forms.

A sixth aspect of the present invention is a method for preparing a wet-granulated composition of atorvastatin comprising:
(a) combining atorvastatin or a pharmaceutically acceptable salt thereof in combination with at least one active drug with sodium starch glycolate, starch, sodium alginate, powdered cellulose, hydroxypropylcellulose, magnesium aluminum silicate or polacrilin potassium or combinations thereof, and optionally other excipients;
(b) adding sufficient water, isopropanol, ethanol, or a mixture thereof to the atorvastatin blend from step (a) under shear to generate granules;
(c) optionally milling or sieving said wet granules;
(d) drying said granules;
(e) optionally milling, grinding or sieving said granules;
(f) optionally mixing in other excipients; and
(g) optionally, forming the composition into unit dosage forms.

A seventh aspect of the present invention is a method for preparing a wet granulated composition of atorvastatin comprising:
(a) combining atorvastatin or a pharmaceutically acceptable salt thereof in combination with at least one active drug with a diluent with less than 2 weight % of a disintegrant;
(b) adding sufficient water, isopropanol, ethanol, or a mixture thereof to the atorvastatin blend from step (a) under shear to generate granules;

(c) optionally milling, grinding or sieving said wet granules;
(d) drying said granules;
(e) optionally milling, grinding or sieving said granules;
(f) mixing in a disintegrant and optionally other excipients; and
(g) optionally, forming the composition into unit dosage forms.

An eighth aspect of the present invention is a method for preparing a wet granulated composition of atorvastatin comprising:
(a) combining atorvastatin or a pharmaceutically acceptable salt thereof in combination with at least one active drug and one or more excipients;
(b) adding, under shear, a sufficient amount of a solution of a volatile base dissolved in water, isopropanol or ethanol or a mixture thereof, to generate granules;
(c) optionally milling, grinding or sieving said wet granules;
(d) drying said granules;
(e) optionally milling, grinding or sieving said granules;
(f) optionally mixing in other excipients as needed to make the final composition; and
(g) optionally, forming said composition into unit dosage forms.

A ninth aspect of the present invention is a kit for achieving a therapeutic effect in a mammal comprising a therapeutically effective amount of tablets or capsules prepared from a wet granulated composition of atorvastatin prepared in the form of unit dosage forms from said compositions and a container for containing said dosage forms.

An tenth aspect of the present invention is a method of using the pharmaceutical composition to treat subjects suffering from hypercholesterolemia and/or hyperlipidemia, osteoporosis, benign prostatic hyperplasia (BPH), and Alzheimer's disease.

DETAILED DESCRIPTION OF THE INVENTION

Atorvastatin can readily be prepared as described in U.S. Pat. Nos. 4,681,893, 5,273,995 and 5,969,156, which are incorporated herein by reference. The hemicalcium salt of atorvastatin is currently sold as Lipitor®.

Atorvastatin exists in a number of morphological forms ranging from highly crystalline forms to forms with varying degrees of disorder. Some of these disordered forms still possess some structure as indicated by powder x-ray patterns. For the purpose of the present invention, all forms of atorvastatin benefit from the invention and are included in the scope of the invention. Less ordered forms of atorvastatin, especially amorphous or predominantly amorphous forms, particularly benefit from the invention. Such forms can be prepared, for example, from the crystalline material using procedures disclosed in U.S. Pat. No. 6,087,511, which is incorporated herein by reference. Alternatively, amorphous atorvastatin material can be prepared according to the processes disclosed in United States Patent Application, commonly owned, (Ser. No. 10/828,488). For the practice of the present invention, non-crystalline and crystalline atorvastatin can be prepared by any method known in the art. The following is a non-exclusive list of patents and published patent applications disclosing preferred forms of atorvastatin for the present invention: U.S. Pat. No. 5,969,156; U.S. Pat. No. 6,121,461; U.S. Pat. No. 6,605,729; International Patent Application WO 01/36384; International Patent Application WO 02/41834; International Patent Application WO 02/43732; International Patent Application WO 02/051804; International Patent Application WO 02/057229; International Patent Application WO 03/011826; International Patent Application WO 03/050085; International Patent Application WO 03/070702; and International Patent Application WO 04/022053. All the above patents and applications are incorporated herein by reference.

The atorvastatin can be used in the form it is prepared, or it can be subjected to a process which changes the physical nature of the particles. For example, the material can be milled by any process known in the art. Non-exclusive examples of such processes include mechanical milling and jet milling. The particles produced either directly from the process of forming non-crystalline atorvastatin or after a milling operation preferably provide average particle diameters in the range of 1-200 µm; more preferably between 5 and 150 µm.

Pharmaceutically acceptable base addition salts of atorvastatin are formed with metals or amines, such as alkaline and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge, S. M., et al., "Pharmaceutical Salts", J. Pharm. Sci., 1977; 66:1).

The base addition salts of atorvastatin are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Additionally, atorvastatin can exist in unsolvated forms as well as solvated forms, including hydrated forms. In general, the solvated forms, including hydrated forms, are intended to be encompassed within the scope of the present invention.

Forms of atorvastatin that are at least somewhat disordered or a mixture of crystalline and disordered forms of atorvastatin benefit most significantly from the present invention. By somewhat disordered, it is meant that the line width (peak width at half the height of the peak) of any of the peaks measured using powder x-ray diffraction (PXRD) have 2 theta values greater than about 2°. Amorphous or predominantly amorphous forms of atorvastatin, which especially benefit from the present invention, are characterized by having very broad, featureless peaks. It should be noted that combinations of crystalline and at least somewhat disordered forms of atorvastatin will show both sharp (i.e., less than 2° values for 2 theta) and broad peaks (i.e., greater than) 2°, and such combinations of forms benefit from the present invention.

Atorvastatin has been found to be an effective drug even at relatively low doses. In fact, by keeping the dose low for a given patient, it is possible to minimize side-effects while still maintaining drug efficacy. It is therefore desirable to provide atorvastatin in a form capable of providing a low dose to the patient. For the purposes of the present invention, the dose provided by the final dosage form of atorvastatin is preferably between 0.5 and 120 mgA (where mgA means milligrams of active drug based on the free acid); more preferably between 5 and 80 mgA.

For convenience and ease of patient compliance, most drugs are delivered in the form of unit dosage forms. For solid drug substances, these unit dosage forms are generally in the form of tablets and capsules. In the present invention, the dosage form is preferably in the form of a capsule or tablet; most preferably in the form of a tablet. The preparation of these forms involves a necessary step of filling a die or capsule with powder. In order for the unit dosages to have the same potency within allowable margins (relative standard deviation, RSD, of less than 6% to meet Stage I, and less than 7.8% to meet Stage II of the United States Pharmacopoeia, USP, guidelines), there must not be any significant segregation of formulation components. For this reason, it can be desirable to granulate atorvastatin, especially when the drug is used at low doses. Wet granulations bind the drug with excipients and thereby minimize any segregation tendency.

The present invention discloses wet granulation processes and formulations that provide atorvastatin in a pure and stable form. The term "impurities" describes materials in the drug substance present from the synthesis and purification process and any drug-based materials formed in the preparation of the unit dosage form. The term "degradants" refers to any drug-based materials generated after the preparation of the unit dosage form (during the shelf-life of the dosage form). Analysis of impurities and degradants is done using reverse phase high performance liquid chromatography, HPLC, techniques on extracted samples as is known in the art. Calculations of the amount of impurities and degradants is expressed as the integrated area percent of all peaks other than the drug peak divided by the integrated area percent of all peaks, or where possible, based on a response factor for integration of peaks from samples of authentic materials.

In the formulation of atorvastatin with a wet granulation, combinations of diluents, binders, disintegrants, lubricants and other additives known in the art are used to provide the properties needed for the unit dosage form as is known in the art. For example, for preparation of tablets, the combination provides for adequate tablet hardness upon compression while providing rapid disintegration in vivo. Although there is a wide degree of latitude in formulating atorvastatin to meet these conditions, typically such tablet formulations contain about 1-40% weight:weight (w:w) drug, about 1-15% disintegrant, about 0-10% binder and about 0.5-2% lubricant, with the bulk comprising a diluent and/or other components. Preferred binders include carboxymethylcellulose, hydroxyethylcellulose, hydroxypropylcellulose, dextrin, gelatin, guar gum, hydroxypropyl methylcellulose, maltodextrin, methylcellulose, polyethylene oxide, polymethacrylates and sodium alginate; a particularly preferred binder is hydroxypropylcellulose. A preferred lubricant is magnesium stearate. Preferred diluents include calcium phosphate, calcium sulfate, cellulose acetate, dextrates, dextrin, dextrose, fructose, kaolin, lactitol, lactose, maltitol, maltodextrin, maltose, microcrystalline cellulose, polymethacrylates, powdered cellulose, silicified microcrystalline cellulose, sodium chloride, sorbitol, sucrose and talc.

In the practice of the present invention, the level of alkaline earth metal salt additives in the composition is preferably about 0-5% (w:w); more preferably, about 0-3%; most preferably about 0-2%. It is also preferred that the level of other alkalizing agent additives in the composition be about 0-5% (w:w); more preferably, about 0-3%; most preferably about 0-2%. It is also preferred that amine polymers and amide polymers be less than about 0-5% (w:w); more preferably, about 0-3%; most preferably about 0-2% of the formulation. Examples of such polymers are disclosed in International Patent Application WO 01/76566A1.

Alkalizing agents are additives or excipients that have the property of increasing the pH of a formulation, when such formulations are added to water. Examples of alkalizing agents include inorganic and organic bases (buffers). Examples of inorganic alkalizing agents include sodium or potassium citrate, carbonate, bicarbonate, phosphate, sulfate, benzoate and ascorbate, and calcium carbonate and magnesium carbonate. The latter two examples also represent alkaline earth metal salts. Examples of organic alkalizing agents include amines. Specific examples of amines include N-methylglucamine, guanine and arginine.

In preparation of atorvastatin compositions by wet granulation, any technique known in the art for wet granulation can be used for the purposes of the present invention. An important element to these processes is that the granulation solution is added to the atorvastatin composition while the powder blend is under shear. The shear serves to break up incipient clumps and thereby provide a more uniform granulation. Non-limiting examples of shearing processes include high shear wet granulations, fluid-bed granulations, extrusion granulations and low shear wet granulations (such as stirrers, mixers and blenders, including bin blenders). The amount of wet granulation solvent added is determined based on adequate wetting to bind the majority of the fine particles. The wet granulation solvent addition can be carried out using any technique known in the art. For example, the liquid can be added in single or multiple rapid additions, sprayed onto a stirring powder bed, pumped directly onto the powder or introduced into fluidizing gas. Mixing times with the liquid are generally optimized such that the majority of fine particles are bound in granules, yet the granules themselves are not over-hardened.

Once the granules are formed, it is sometimes advantageous to mill, grind or sieve the material while it is wet (softened), as is known in the art. The wet composition is preferably dried before use in formation of unit dosage forms. Such drying can be accomplished using any method known in the art. Non-limiting examples of these methods include air drying, fluid bed drying, microwave drying, oven drying, radio frequency drying vacuum oven drying and convection oven drying. We have found that the drying temperature is important to control to provide low levels of atorvastatin impurities. Preferably the drying temperature does not exceed about 60° C.; more preferably, the temperature does not exceed about 50° C.; most preferably, the temperature does not exceed about 40° C. Once the granules are dry, it is sometimes desirable to reduce the particle size by milling, grinding or sieving, as is known in the art. After this point, a lubricant is typically added followed by a short (about 1-10 minute) mixing period, typically carried out in a low shear blender such as a tumbling blender. Examples of said tumbling blenders include bin-blenders, V-blenders and Turbula™ blenders. The preferred lubricant is magnesium stearate. Once the blend is made, unit dosage forms are prepared by procedures known in the art. Preferable the unit dosage forms include tablets or capsules. Tablets are made by filling a die with the atorvastatin containing composition, then pressing with a matching punch. Capsules are prepared by filling shaped capsule shells then sealing. Such operations are preferably carried out using a rotary tablet press or commercial capsule-filling machine. Non-exclusive examples of commercial rotary tablet presses include those produced by Niro Pharma Systems (Columbia, Md.), Kilian and Company (Horsham, Pa.), Korsch (Berlin, Germany) and Elizabet-Hata International (North Huntingdon, Pa.). Non-exclusive examples of commercial capsule filling equipment include those made by Capsugel (Morris Plains, N.J.) and CapPlus Technologies (Phoenix, Ariz.). Tablets thus prepared can then optionally be coated with a film designed to provide ease of swallowing, a proprietary or identification appearance and/or protection of the dosage form. The final unit dosage form is then packaged using procedures known in the art. For the present invention, the packaging is preferably in the form of foil-foil cold form blisters, plastic blisters or sealed bottles containing desiccants. Optionally, the packaging can contain active oxygen absorbing materials as is disclosed in EP1243524A2 or EP1241110A1, which are incorporated herein by reference.

Atorvastatin undergoes two major degradation pathways: lactonization and oxidation. The lactone is formed by internal condensation (loss of water) of the alcohol and carboxylic acid to form a six-membered ring. This is the major degradant of atorvastatin found upon wet granulation and tablet formation, especially in the absence of alkaline earth metal salts. We have found that the level of the lactone in tablets prepared by wet granulation with less than 5% (w:w) of an alkaline earth metal salt additive can be significantly reduced by a combination of the choice of excipients and the wet granulation process.

When atorvastatin is prepared in the form of a tablet, a disintegrant is desirable to provide for rapid disintegration of the tablet in the gastrointestinal tract and thereby assure that the drug is rapidly available for absorption. A large number of disintegrants are disclosed in the prior art for use with atorvastatin. For example, the following list of disintegrants is disclosed in International Patent Publication Number WO03/011283A1 in combination with an alkalizing agent and a second active pharmaceutical ingredient: calcium carboxymethylcellulose, sodium carboxymethylcellulose, silica, croscarmellose sodium, crospovidone, guar gum, magnesium aluminum silicate, methylcellulose, polacrilin potassium, cellulose, pregelatinized starch, sodium alginate, sodium starch glycolate and starch. In a number of patents, the examples have focused on use of croscarmellose sodium (see for example U.S. Pat. Nos. 5,686,014, 6,126,971, 6,531,507B1, and Published European Patent Application EP1336405A1). This disintegrant is also used in the commercial product Lipitor®. While many of these disintegrants provide for adequate disintegration properties, in wet granulations of atorvastatin with less than 5% (w:w) alkalizing agent additives, we have unexpectedly determined that only some of the many possible disintegrants provide for adequate drug purity. In fact, the disintegrant used in the majority of examples (croscarmellose sodium), was unexpectedly found to provide poor drug purity.

Preferred disintegrants provide atorvastatin formulations with a level of atorvastatin lactone less than about 3% (based on area percent of the lactone peak compared to all drug-related peaks by HPLC integration) after wet granulation and drying; more preferred disintegrants provide lactone levels less than about 1%; and still more preferred disintegrants provide lactone levels less than about 0.5%.

Disintegrants suitable for the current invention also provide for disintegration times of tablets produced therein of preferably less than 30 minutes; still more preferably less than 15 minutes; and still more preferably less than 8 minutes. Disintegration times are measured using pH 6.8 phosphate buffer solutions with commercially available disintegration measurement devices.

Preferred disintegrants for compositions useful for wet granulation of atorvastatin with less than about 5 weight % alkalizing agent additives or alkaline earth metal salts include starches, sodium starch glycolate, sodium alginate, powdered cellulose, hydroxypropylcellulose, magnesium aluminum silicate and polacrilin potassium. Particularly preferred starches include cornstarch and pregelatinized starch. These disintegrants are preferably used in compositions of atorvastatin at levels between about 1 and about 10% (w:w) of the overall formulation; more preferably between about 3 and about 8% (w:w).

Preferred wet granulation solvents have the property of inducing adhesion between particles without significant dissolution of the atorvastatin, which could cause the drug to change morphological forms. In addition, it is preferable that such solvents be volatile and of low toxicity such that any trace amount remaining will not be harmful. As such, preferred granulation solvents for atorvastatin are water and alcohols. Particularly preferred alcohols are ethanol and isopropanol. In many cases, combinations of solvents can be advantageous. Preferably such combinations involve water with ethanol or isopropanol. In addition, it can be advantageous to add ingredients to the granulation solvent, as is known in the art. For example, binding agents, wetting agents and stabilizers can be incorporated as part of the granulation solvent and are within the scope of the present invention.

We have found that a particular additive to the granulation solvent, the wetting agent TWEEN™ 80 (polysorbate 80) is detrimental to the stability of the atorvastatin. This is surprising since this additive is commonly used in most prior art formulations of atorvastatin (see for example, U.S. Pat. Nos. 5,686,104 and 6,126,971). Therefore, it is preferable that the level of TWEEN™ 80 (polysorbate 80) used in wet granulated compositions of atorvastatin be less than 0.5% (w:w); more preferably less than 0.2%; and still more preferably, less than 0.1%.

Preferred processes for preparing a wet granulation of atorvastatin with less than about 5 weight % alkalizing agent additives or alkaline earth metal salts with preferred disintegrants comprise the following steps:

(a) blending of the atorvastatin with a preferred disintegrant and optionally some or all of the remaining excipients needed for the final composition. These other excipients can include diluents, binders and other such materials necessary for processing, flow, stability or formation of unit dosage forms;

(b) adding a granulation solvent while the material from step (a) is under shear. Preferred granulation solvents include, water, ethanol, isopropanol and combinations thereof. Other ingredients can be added to the granulation solvent as is known in the art. Examples of such additives are binders, wetting agents, stabilizers and buffers. The solvent can be applied by any technique known in the art. Preferred methods of applying the solvent while imparting shear include high shear granulation, low shear granulation, fluid bed granulation and extrusion granulation;

(c) optionally, the material from step (b) can be milled, ground or sieved. This wet material is then dried, preferably using air drying, fluid bed drying, oven drying or microwave drying. The drying is preferably carried out such that the drying temperature does not exceed about 60° C.; more preferably, the temperature does not exceed about 50° C.; most preferably, the temperature does not exceed about 40° C.;

(d) optionally this material is then milled or sieved;

(e) the material is then blended with additional excipients; and (f) the composition is optionally formed into a unit dosage form, preferably a tablet or a capsule.

We have also found that even when using disintegrants that induce lactonization of the drug (in the absence of base) during a wet granulation, it is possible to incorporate such excipients by a change in the process for addition of the disintegrant. More specifically, we have found that adding disintegrants to the composition subsequent to the wet granulation step, that is, in an extragranular addition, provides for unexpected improvement in the drug stability. The preferred steps in this process comprise:

(a) blending of the atorvastatin with at least some of the excipients needed for the final composition, but with no significant amount of a disintegrant. A significant amount of disintegrant is considered greater than about 2% (w:w) of the formulation. Other excipients can include diluents, binders and other such materials necessary for processing, flow, stability or formation of unit dosage forms;

(b) adding a granulation solvent while the material from step (a) is under shear. Preferred granulation solvents include water, ethanol and isopropanol and combinations thereof. Other ingredients can be added to the granulation solvent as is known in the art. Examples of such additives are binders, wetting agents, stabilizers and buffers. The liquid can be applied by any technique known in the art. Preferred methods of applying the liquid while imparting shear include high shear granulation, low shear granulation, fluid bed granulation and extrusion granulation;

(c) optionally, the material from step (b) can be milled, ground or sieved. This wet material is then dried, preferably using air drying, fluid bed drying, oven drying or microwave drying; such drying is preferably carried out such that the drying temperature does not exceed about 60° C.; more preferably, the temperature does not exceed about 50° C.; most preferably, the temperature does not exceed about 40° C.;

(d) optionally this material is then milled, ground or sieved;

(e) this composition is then blended with one or more disintegrants and optionally additional excipients, preferably including a lubricant, and (f) the final composition is optionally formed into a unit dosage form, preferably a tablet or a capsule.

We have also found another process for improving drug purity for a wet granulation of atorvastatin, even in the presence of disintegrants showing poor drug purity. More specifically, we have unexpectedly found that having a base present in a composition only during the wet granulation and drying processes provides for stabilization of atorvastatin against lactonization, even though the base is not present in the final product. In particular, volatile bases were found to provide wet granulations of atorvastatin in the absence of other added bases with a higher degree of purity than in the absence of such volatile bases. Examples of such preferred volatile bases include ammonium hydroxide, tetraalkylammonium hydroxides, secondary and tertiary alkyl and aryl amines, diethanolamine and monoethanolamine. Particularly preferred volatile bases include ammonium hydroxide and tetrabutyl ammonium hydroxide. These bases can be added with the granulation solvent (preferably water, isopropanol, ethanol, or combination thereof) at a level selected to be effective at providing good purity and stability for the final atorvastatin dosage form without themselves inducing drug degradation or discoloration of the formulation. We have found that the concentration of volatile base used in the granulation water preferably ranges between about 0.001 and about 50% (w:w); more preferably, between about 0.1 and about 40% (w:w). The amount of granulation solution of base added to the granulation preferably is between about 40 and about 100% (w:w) of the solid material.

The present invention provides for compositions of atorvastatin which are particularly well suited for combination products with other drug substances because of the greater atorvastatin stability imparted by the disintegrants of the present invention. This is especially true when the second drug (with its associated excipients) can destabilize atorvastatin. Non-limiting examples of drugs which may benefit from combinations with the inventive atorvastatin compositions and processes include torcetrapib and amlodipine and its pharmaceutically acceptable salts.

Compositions of atorvastatin according to the present invention can be combined with a least one other active drug to form unit dosage forms. Preferred unit dosage forms include tablets and capsules. In the combination of the atorvastatin composition with at least one other active drug to form a unit dosage form, the following non-limiting list describes options for such unit dosage forms: (a) a blend of wet-granulated atorvastatin with the other active drug itself (i.e., extragranular addition of the other drug to the wet granulated atorvastatin), as a blend with excipients (i.e., extragranular addition of the other drug plus excipients to the wet granulated atorvastatin), or as a granulation (i.e., combination of the other drug granulation with the wet granulated atorvastatin), formed into tablets or capsules; (b) a single wet granulation of atorvastatin with the other drug, formed into tablets of capsules; (c) a bilayer tablet comprising wet granulated atorvastatin in one layer and the other drug and optional excipients in the other layer.

The present invention relates to the treatment of diseases and conditions in a subject, such as, hyperlipidemia and/or hypercholesterolemia, osteoporosis, benign prostatic hyperplasia (BPH), and Alzheimer's disease with atorvastatin or a pharmaceutically acceptable salt thereof as described above that may be administered in a unit dosage form having low levels of degradation products and/or impurities contained in a therapeutic package or kit. The kit includes the unit dosage form and a container. Typically, the kit includes directions for administration of the dosage form. The container can be in any conventional shape or form as known in the art, for example, a paper box, a glass or plastic bottle, or a blister pack with individual dosage forms pressing out of the back according to a therapeutic schedule.

The following non-limiting examples illustrate the inventors' preferred methods for preparing and using the pharmaceutical compositions of the present invention.

Example 1

General Method for Preparation of Amorphous Atorvastatin

Amorphous atorvastatin, an example of disordered atorvastatin as previously described and used in the following examples was prepared according to the process disclosed in concurrently filed U.S. Patent Application, commonly owned, Ser. No. 10/828,488, by first dissolving atorvastatin calcium (U.S. Pat. No. 5,273,995) in methanol to make a 5% (w:w) solution. This solution was sprayed into a Niro PSD-1 spray dryer at a rate of 170 gram/minute (g/min) using nitrogen as the atomizing gas. The inlet temperature was 195° C. and the outlet temperature was 60° C. After spray drying, the powder was tray-dried in an oven at 40° C. for 12 hrs to afford amorphous atorvastatin.

Example 2

Preparation of Amorphous Atorvastatin Calcium Tablets Using a Wet Granulation without a Disintegrant Amorphous atorvastatin calcium, prepared as described in Example 1 (1.3 g), 39.0 g of microcrystalline cellulose (Avicel PH102™, FMC Biopolymer, Philadelphia, Pa.), 50.7 g of lactose, hydrous (Foremost Farms USA, Rothschild, Wis.), and 2.0 g of hydroxypropyl cellulose (Klucel EXF™, Hercules Incorporated, Aqualon Division, Wilmington, Del.) were combined in a 500-cc bottle and mixed for 10 min. using a Turbula Shaker Mixer (Willy A. Bachofen AG Maschinenfabrik, Basel, Switzerland). The formulation was then granulated using a Pro-C-epT Mi Mi Pro high shear wet granulator (Pro-C-epT n.v., B-9060 Zelzate, Belgium) using a 0.9 L bowl. The formulation was dry-mixed for 2 min. at an impeller speed of 400 revolutions per minute (rpm) and chopper speed of 1000 rpm. Wet mixing was done at a 600-rpm impeller speed and 1000-rpm chopper speed. Water was added in increments of 10-30 g at 20-30 g/min. for a total of 45 g using a standard 60-cc syringe. The material was wet-mixed for a total of 2.5 min. The granulation was wet sieved through a #10 mesh sieve by hand to achieve a more uniform granule size before drying. The granulation was tray-dried overnight at 50° C. for 16 hrs. in a forced hot air dryer (Gruenberg Forced Hot Air Oven, Gruenberg Oven Co., Williamsport, Pa.). The granulation was then milled using a Fitzpatrick L1A mill (Fitzpatrick Co., Elmhurst, Ill.) with a 0.040" Conidur rasping plate at 500 rpm. Material was analyzed for the level of atorvastatin lactone (based on the ratio of lactone peak integration compared to the total peak integrated areas using HPLC) by adding 400 mg of the granulation to 50 mL of 1:1 (v:v) of 0.05M ammonium citrate buffer (pH 7.4):acetonitrile and shaking for 20 min. The material was then filtered using a Gelman Acrodisc polytetrafluoroethylene membrane (0.45 µm pore size), and analyzed using high-pressure liquid chromatography (HPLC) (Phenomenex, Ultremex C18 column, 5 µm particle size, 25.0 cm×4.6 mm, HPLC Waters 2690D, Waters Corp., Milford, Mass., 20 µl injection volume, flow of 1.5 mL/min; mobile phase of 53:27:20 (v:v:v) 0.05M ammonium citrate (pH 4.0):acetonitrile:tetrahydrofuran; detection using a Waters 2487 detector at 244 nm). Results are reported in Table 1. Tablets were made under manual power using a single station Manesty F-Press (Manesty, Liverpool, United Kingdom). A ¹³⁄₃₂" standard round concave (SRC) punch and die was used to produce tablets with weights of 450 mg each. The target tablet hardness was 12 kP with a range of 10-14 kP (tablet hardness was tested using a Schleuniger Tablet Hardness Tester, Dr. Schleuniger Pharmatron AG, Solothurn, Switzerland).

Example 3

Preparation of Amorphous Atorvastatin Calcium Using a Wet Granulation with Croscarmellose Sodium Amorphous atorvastatin calcium, prepared as described in Example 1 (1.3 g), 39.0 g of microcrystalline cellulose (Avicel PH102™, FMC Biopolymer, Philadelphia, Pa.), 50.7 g of lactose, hydrous (Foremost Farms USA, Rothschild, Wis.), 3.0 g of croscarmellose sodium (Ac-Di-Sol™, FMC Biopolymer, Philadelphia, Pa.) and 2.0 g of hydroxypropyl cellulose (Klucel EXF™, Hercules Incorporated, Aqualon Division, Wilmington, Del.) were combined in a 500-cc bottle and mixed for 10 min. using a Turbula Shaker Mixer (Willy A. Bachofen AG Maschinenfabrik, Basel, Switzerland). The formulation was then granulated using a Pro-C-epT Mi Mi Pro high shear wet granulator (Pro-C-epT n.v., B-9060 Zelzate, Belgium) using a 0.9 L bowl. The formulation was dry-mixed for 2 min. at an impeller speed of 400 rpm and chopper speed of 1000 rpm. Wet mixing was done at a 600-rpm impeller speed and 1000-rpm chopper speed. Water was added in increments of 10-30 g at 20-30 g/min. for a total of 60 g using a standard 60-cc syringe. The material was wet-mixed for a total of 5.5 min. The granulation was wet sieved through a #10 mesh sieve by hand to achieve a more uniform granule size before drying. The granulation was tray-dried overnight at 50° C. for 16 hrs. in a forced hot air dryer (Gruenberg Forced Hot Air Oven, Gruenberg Oven Co., Williamsport, Pa.). The granulation was then milled using a Fitzpatrick L1A mill with a 0.040" Conidur rasping plate at 500 rpm. Material was analyzed as described in Example 2, and results are reported in Table 1.

Example 4

Preparation of Amorphous Atorvastatin Calcium Using a Wet Granulation with Sodium Starch Glycolate Amorphous atorvastatin calcium, prepared as described in Example 1 (1.3 g), 39.0 g of microcrystalline cellulose (Avicel PH102™, FMC Biopolymer, Philadelphia, Pa.), 50.7 g of lactose, hydrous (Foremost Farms USA, Rothschild, Wis.), 3.0 g of sodium starch glycolate, (Explotab™, Penwest Pharmaceuticals Co., Cedar Rapids, Iowa) and 2.0 g of hydroxypropyl cellulose (Klucel EXF™, Hercules Incorporated, Aqualon Division, Wilmington, Del.) were combined in a 500-cc bottle and mixed for 10 min. using a Turbula Shaker Mixer (Willy A. Bachofen AG Maschinenfabrik, Basel, Switzerland). The formulation was then granulated using a Pro-C-epT Mi Mi Pro high shear wet granulator (Pro-C-epT n.v., B-9060 Zelzate, Belgium) using a 0.9 L bowl. The formulation was dry-mixed for 2 min. at an impeller speed of 400 rpm and chopper speed of 1000 rpm. Wet mixing was done at a 600-rpm impeller speed and 1000-rpm chopper speed. Water was added in increments of 10-30 g at 20-30 g/min. for a total of 55 g using a standard 60-cc syringe. The material was wet-mixed for a total of 5.5 min. The granulation was wet sieved through a #10 mesh sieve by hand to achieve a more uniform granule size before drying. The granulation was tray-dried overnight at 50° C. for 16 hrs. in a forced hot air dryer (Gruenberg Forced Hot Air Oven, Gruenberg Oven Co., Williamsport, Pa.). The granulation was then milled using a Fitzpatrick L1A mill with a 0.040" Conidur rasping plate at 500 rpm. Material was analyzed as described in Example 2, and results are reported in Table 1.

Example 5

Preparation of Amorphous Atorvastatin Calcium Using a Wet Granulation with Corn Starch Amorphous atorvastatin calcium, prepared as described Example 1 (1.3 g), 39.0 g of microcrystalline cellulose (Avicel PH102™, FMC Biopolymer, Philadelphia, Pa.), 50.7 g of lactose, hydrous (Foremost Farms USA, Rothschild, Wis.), 3.0 g of corn starch—Purity 21 (National Starch and Chemical Corp., Bridgewater, N.J.) and 2.0 g of hydroxypropyl cellulose (Klucel EXF™, Hercules Incorporated, Aqualon Division, Wilmington, Del.) were combined in a 500-cc bottle and mixed for 10 min. using a Turbula Shaker Mixer (Willy A. Bachofen AG Maschinenfabrik, Basel, Switzerland). The formulation was then granulated using a Pro-C-epT Mi Mi Pro high shear wet granulator (Pro-C-epT n.v., B-9060 Zelzate, Belgium) using a 0.9 L bowl. The formulation was dry-mixed for 2 min. at an impeller speed of 400 rpm and chopper speed of 1000 rpm. Wet mixing was done at a 600-rpm impeller speed and 1000-rpm chopper speed. Water was added in increments of 10-30 g at 20-30 g/min. for a total of 45 g using a standard 60-cc syringe. The material was wet-mixed for a total of 2.5 min. The granulation was wet sieved through a #8 mesh sieve by hand to achieve a more uniform granule size before drying. The granulation was tray-dried overnight at 50° C. for 16 hrs. in a forced hot air dryer (Gruenberg Forced Hot Air Oven, Gruenberg Oven Co., Williamsport, Pa.). The granulation was then milled using a Fitzpatrick L1A mill with a 0.040" Conidur rasping plate at 500 rpm. Material was analyzed as described in Example 2, and results are reported in Table 1.

Example 6

Preparation of Amorphous Atorvastatin Calcium Using a Wet Granulation with Pregelatinized Starch Amorphous atorvastatin calcium, prepared as described in Example 1 (1.3 g), 39.0 g of microcrystalline cellulose (Avicel PH102™, FMC Biopolymer, Philadelphia, Pa.), 50.7 g of lactose, hydrous (Foremost Farms USA, Rothschild, Wis.), 3.0 g of pregelatinized starch (Starch 1500, Colorcon, West Point, Pa.) and 2.0 g of hydroxypropyl cellulose (Klucel EXF™, Hercules Incorporated, Aqualon Division, Wilmington, Del.) were combined in a 500-cc bottle and mixed for 10 min. using a Turbula Shaker Mixer (Willy A. Bachofen AG Maschinenfabrik, Basel, Switzerland). The formulation was then granulated using a Pro-C-epT Mi Mi Pro high shear wet granulator (Pro-C-epT n.v., B-9060 Zelzate, Belgium) using a 0.9 L bowl. The formulation was dry-mixed for 2 min. at an impeller speed of 400 rpm and chopper speed of 1000 rpm. Wet mixing was done at a 600-rpm impeller speed and 1000-rpm chopper speed. Water was added in increments of 10-30 g at 20-30 g/min. for a total of 40 g using a standard 60-cc syringe. The material was wet-mixed for a total of 3 min. The granulation was wet sieved through a #8 mesh sieve by hand to achieve a more uniform granule size before drying. The granulation was tray-dried overnight at 50° C. for 16 hrs. in a forced hot air dryer (Gruenberg Forced Hot Air Oven, Gruenberg Oven Co., Williamsport, Pa.). The granulation was then milled using a Fitzpatrick L1A mill with a 0.040" Conidur rasping plate at 500 rpm. Material was analyzed as described in Example 2, and results are reported in Table 1.

Example 7

Preparation of Amorphous Atorvastatin Using a Wet Granulation with Sodium Alginate Amorphous atorvastatin calcium, prepared as described in Example 1 (40.5 mg), 1.22 g of microcrystalline cellulose (Avicel PH102™, FMC Biopolymer, Philadelphia, Pa.), 1.58 g of lactose, hydrous (Foremost Farms USA, Rothschild, Wis.), 93.9 mg of sodium alginate (Protanal™, FMC BioPolymer, Philadelphia, Pa.) and 62.4 mg of hydroxypropyl cellulose (Klucel EXF™, Hercules Incorporated, Aqualon Division, Wilmington, Del.) were combined in a 30-cc bottle and mixed for 10 min. using a Turbula Shaker Mixer (Willy A. Bachofen AG Maschinenfabrik, Basel, Switzerland). The mixture was then granulated in the 30-cc bottle, using a bent micro-spatula impeller with a ½" blade on a variable speed mini-drill press (Micro-Drill model 164C-7, Cameron Precision Engineering Co., Sonora, Calif. 95370). Prior to use, the blade was bent to an angle sufficient to sweep the material being granulated, and to allow a portion of this material to flow over the top of the blade. The blade was bent to an angle about 30° from vertical. The granulating fluid was pipetted in 1.0 to 0.5 mL increments, wet mixing for 2.5 min. until a suitable granulation was formed based upon visual observations (total of 1.5 mL added). The granulation was tray-dried for 16 hrs at 50° C. in a forced hot air dryer (Gruenberg Forced Hot Air Oven, Gruenberg Oven Co., Williamsport, Pa.). Material was analyzed as described in Example 2, and results are reported in Table 1.

Example 8

Preparation of Amorphous Atorvastatin Calcium Using a Wet Granulation with Alginic Acid Amorphous atorvastatin calcium, prepared as described in Example 1 (40.5 mg), 1.22 g of microcrystalline cellulose (Avicel PH102™, FMC Biopolymer, Philadelphia, Pa.), 1.58 g of lactose, hydrous (Foremost Farms USA, Rothschild, Wis.), 93.9 mg of alginic acid (Protacid™, FMC BioPolymer, Philadelphia, Pa.) and 62.4 mg of hydroxypropyl cellulose (Klucel EXF™, Hercules Incorporated, Aqualon Division, Wilmington, Del.) were combined in a 30-cc bottle and mixed for 10 min. using a Turbula Shaker Mixer (Willy A. Bachofen AG Maschinenfabrik, Basel, Switzerland). The mixture was then granulated in the 30-cc bottle, using a bent micro-spatula impeller with a ½" blade on a variable speed mini-drill press (Micro-Drill model 164C-7, Cameron Precision Engineering Co., Sonora, Calif. 95370). Prior to use, the blade was bent to an angle sufficient to sweep the material being granulated, and to allow a portion of this material to flow over the top of the blade. The blade was bent to an angle about 30° from vertical. The granulating fluid was pipetted in 1.0 to 0.5 mL increments, wet mixing for 2.5 min. until a suitable granulation was formed based upon visual observations (total of 1.5 mL added). The granulation was tray-dried for 16 hrs at 50° C. in a forced hot air dryer (Gruenberg Forced Hot Air Oven, Gruenberg Oven Co., Williamsport, Pa.). Material was analyzed as described in Example 2, and results are reported in Table 1.

Example 9

Preparation of Amorphous Atorvastatin Calcium Using a Wet Granulation with Powdered Cellulose Amorphous atorvastatin calcium, prepared as described in Example 1 (40.5 mg), 1.22 g of microcrystalline cellulose (Avicel PH102™, FMC Biopolymer, Philadelphia, Pa.), 1.58 g of lactose, hydrous (Foremost Farms USA, Rothschild, Wis.), 93.9 mg of powdered cellulose (Solka-Floc 40NF™, International Fiber Corp., North Tonawanda, N.Y.) and 62.4 mg of hydroxypropyl cellulose (Klucel EXF™, Hercules Incorporated, Aqualon Division, Wilmington, Del.) were combined in a 30-cc bottle and mixed for 10 min. using a Turbula Shaker Mixer (Willy A. Bachofen AG Maschinenfabrik, Basel, Switzerland). The mixture was then granulated in the 30-cc bottle, using a bent micro-spatula impeller with a ½" blade on a variable speed mini-drill press (Micro-Drill model 164C-7, Cameron Precision Engineering Co., Sonora, Calif. 95370). Prior to use, the blade was bent to an angle sufficient to sweep the material being granulated, and to allow a portion of this material to flow over the top of the blade. The blade was bent to an angle about 30° from vertical. The granulating fluid was pipetted in 1.0 to 0.5 mL increments, wet mixing for 2.5 min. until a suitable granulation was formed based upon visual observations (total of 1.5 mL added). The granulation was tray-dried for 16 hrs at 50° C. in a forced hot air dryer (Gruenberg Forced Hot Air Oven, Gruenberg Oven Co., Williamsport, Pa.). Material was analyzed as described in Example 2, and results are reported in Table 1.

Example 10

Preparation of Amorphous Atorvastatin Calcium Using a Wet Granulation with Hydroxypropylcellulose Amorphous atorvastatin calcium, prepared as described in Example 1 (40.5 mg), 1.22 g of microcrystalline cellulose (Avicel PH102™, FMC Biopolymer, Philadelphia, Pa.), 1.58 g of lactose, hydrous (Foremost Farms USA, Rothschild, Wis.), 93.9 mg of hydroxypropylcellulose (low substitution grade, Shin-Etsu Chemical Co., Tokyo, Japan) and 62.4 mg of hydroxypropyl cellulose (Klucel EXF™, Hercules Incorporated, Aqualon Division, Wilmington, Del.) were combined in a 30-cc bottle and mixed for 10 min. using a Turbula Shaker Mixer (Willy A. Bachofen AG Maschinenfabrik, Basel, Switzerland). The mixture was then granulated in the 30-cc bottle, using a bent micro-spatula impeller with a ½" blade on a variable speed mini-drill press (Micro-Drill model 164C-7, Cameron Precision Engineering Co., Sonora, Calif. 95370). Prior to use, the blade was bent to an angle sufficient to sweep the material being granulated, and to allow a portion of this material to flow over the top of the blade. The blade was bent to an angle about 30° from vertical. The granulating fluid was pipetted in 1.0 to 0.5 mL increments, wet mixing for 2.5 min. until a suitable granulation was formed based upon visual observations (total of 1.5 mL added). The granulation was tray-dried for 16 hrs at 50° C. in a forced hot air dryer (Gruenberg Forced Hot Air Oven, Gruenberg Oven Co., Williamsport, Pa.). Material was analyzed as described in Example 2, and results are reported in Table 1.

Example 11

Preparation of Amorphous Atorvastatin Calcium Using a Wet Granulation with Magnesium Aluminum Silicate Amorphous atorvastatin calcium, prepared as described in Example 1 (40.5 mg), 1.22 g of microcrystalline cellulose (Avicel PH102™, FMC Biopolymer, Philadelphia, Pa.), 1.58 g of lactose, hydrous (Foremost Farms USA, Rothschild, Wis.), 93.9 mg of magnesium aluminum silicate (Veegum F™, R.T. Vanderbilt Co., Norwalk, Conn.) and 62.4 mg of hydroxypropyl cellulose (Klucel EXF™, Hercules Incorporated, Aqualon Division, Wilmington, Del.) were combined in a 30-cc bottle and mixed for 10 min. using a Turbula Shaker Mixer (Willy A. Bachofen AG Maschinenfabrik, Basel, Switzerland). The mixture was then granulated in the 30-cc bottle, using a bent micro-spatula impeller with a ½" blade on a variable speed mini-drill press (Micro-Drill model 164C-7, Cameron Precision Engineering Co., Sonora, Calif. 95370). Prior to use, the blade was bent to an angle sufficient to sweep the material being granulated, and to allow a portion of this material to flow over the top of the blade. The blade was bent to an angle about 30° from vertical. The granulating fluid was pipetted in 1.0 to 0.5 mL increments, wet mixing for 2.5 min. until a suitable granulation was formed based upon visual observations (total of 1.5 mL added). The granulation was tray-dried for 16 hrs at 50° C. in a forced hot air dryer (Gruenberg Forced Hot Air Oven, Gruenberg Oven Co., Williamsport, Pa.). Material was analyzed as described in Example 2, and results are reported in Table 1.

Example 12

Preparation of Amorphous Atorvastatin Calcium Using a Wet Granulation with Polacrilin Potassium Amorphous atorvastatin calcium, prepared as described in Example 1 (40.5 mg), 1.22 g of microcrystalline cellulose (Avicel PH102™, FMC Biopolymer, Philadelphia, Pa.), 1.58 g of lactose, hydrous (Foremost Farms USA, Rothschild, Wis.), 93.9 mg of polacrilin potassium (Amberlite IRP88™, Rohm and Haas Co., Philadelphia, Pa.) and 62.4 mg of hydroxypropyl cellulose (Klucel EXF™, Hercules Incorporated, Aqualon Division, Wilmington, Del.) were combined in a 30-cc bottle and mixed for 10 min. using a Turbula Shaker Mixer (Willy A. Bachofen AG Maschinenfabrik, Basel, Switzerland). The mixture was then granulated in the 30-cc bottle, using a bent micro-spatula impeller with a ½" blade on a variable speed mini-drill press (Micro-Drill model 164C-7, Cameron Precision Engineering Co., Sonora, Calif. 95370). Prior to use, the blade was bent to an angle sufficient to sweep the material being granulated, and to allow a portion of this material to flow over the top of the blade. The blade was bent to an angle about 30° from vertical. The granulating fluid was pipetted in 1.0 to 0.5 mL increments, wet mixing for 2.5 min. until a suitable granulation was formed based upon visual observations (total of 1.5 mL added). The granulation was tray-dried for 16 hrs at 50° C. in a forced hot air dryer (Gruenberg Forced Hot Air Oven, Gruenberg Oven Co., Williamsport, Pa.). Material was analyzed as described in Example 2, and results are reported in Table 1.

TABLE 1

Effect on drug purity of material formed by wet granulations of atorvastatin with intragranular disintegrants.

| Example No. | Disintegrant | % Atorvastatin Lactone (as determined by HPLC) |
|---|---|---|
| 2 | control (no disintegrant) | 0.21 |
| 3 | croscarmellose sodium | 5.47 |
| 4 | sodium starch glycolate | 0.41 |
| 5 | corn starch | 0.25 |
| 6 | pregelatinized starch | 0.20 |
| 7 | sodium alginate | 0.52 |
| 8 | alginic acid | 15.71 |
| 9 | powdered cellulose | 0.41 |
| 10 | hydroxypropylcellulose | 0.38 |
| 11 | magnesium aluminum silicate | 0.12 |
| 12 | polacrilin potassium | 0.29 |

Example 13

Preparation of Wet Granulations of Atorvastatin and Tablets Thereof with Process Providing Pure Atorvastatin with Range of Disintegrants To 13.30 g of material prepared in Example 2 was added 0.858 g of one of the following disintegrants: (a) sodium starch glycolate; (b) croscarmellose sodium; (c) corn starch, or (d) pregelatinized starch in a 60-cc bottle. The blends were mixed for 5 min. using a Turbula Shaker Mixer. To this blend was added, in each case, 0.143 g of magnesium stearate (Mallinckrodt Co., St. Louis, Mo.). The formulations were then blended 3 min. using a Turbula Shaker Mixer. Material was analyzed for the level of lactone as described in Example 2 and results are reported in Table 2. Tablets were made under manual power using a single station Manesty F-Press (Manesty, Liverpool, United Kingdom). A ¹³⁄₃₂" SRC punch and die was used to produce tablets with weights of 450 mg each. The target tablet hardness was 12 kP with a range of 10-14 kP (tablet hardness was tested using a Schleuniger Tablet Hardness Tester, Dr. Schleuniger Pharmatron AG, Solothurn, Switzerland). Material was analyzed a described in Example 2 and results are reported in Table 2.

TABLE 2

Unexpected beneficial effect on drug purity for wet granulations of atorvastatin with extragranular disintegrants.

| Example | Disintegrant | % Atorvastatin Lactone (as determined by HPLC) |
| --- | --- | --- |
| 2 | control, no disintegrant | 0.21 |
| 13a | sodium starch glycolate | 0.25 |
| 13b | croscarmellose sodium | 0.24 |
| 13c | corn starch | 0.24 |
| 13d | pregelatinized starch | 0.24 |

Example 14

Control of Wet Granulation of Atorvastatin with No Volatile Base

Amorphous atorvastatin calcium prepared as described in Example 1 (62.1 mg), 1772.1 mg of microcrystalline cellulose (Avicel PH102™, FMC Biopolymer, Philadelphia, Pa.), 1010.4 mg of lactose, hydrous (Foremost Farms USA, Rothschild, Wis.), 62.1 mg of hydroxypropyl cellulose (Klucel EXF™, Hercules Incorporated, Aqualon Division, Wilmington, Del.), and 93.3 mg of croscarmellose sodium (Ac-Di-Sol™, FMC Biopolymer, Philadelphia, Pa.) were placed in a 30-cc glass bottle. The combined dry components were mixed for 10 min. using a Turbula Shaker Mixer (Willy A. Bachofen AG Maschinenfabrik, Basel, Switzerland). The mixture was then granulated in the 30-cc bottle, using a bent micro-spatula impeller with a ½" blade on a variable speed mini-drill press (Micro-Drill model 164C-7, Cameron Precision Engineering Co., Sonora, Calif. 95370). Prior to use, the blade was bent to an angle sufficient to sweep the material being granulated, and to allow a portion of this material to flow over the top of the blade. The blade was bent to an angle about 30° from vertical. The granulating fluid was pipetted in 0.5 to 1.0 mL increments, wet mixing for 4 min. until a suitable granulation was formed based upon visual observations (total of 2.5 mL added). The wet granulation was dried overnight at 50° C. for 16 hr. in a forced hot air tray dryer. Material was analyzed for the level of lactone as described in Example 2, with the modification of using 275 mg granulation instead of 400 mg. Results are reported in Table 3.

Example 15

Preparation of Wet Granulations of Amorphous Atorvastatin with Volatile Bases

Amorphous atorvastatin calcium prepared as described in Example 1 (62.1 mg), 1772.1 mg of microcrystalline cellulose (Avicel PH102™, FMC Biopolymer, Philadelphia, Pa.), 1010.4 mg of lactose, hydrous (Foremost Farms USA, Rothschild, Wis.), 62.1 mg of hydroxypropyl cellulose (Klucel EXF™, Hercules Incorporated, Aqualon Division, Wilmington, Del.), and 93.3 mg of croscarmellose sodium (Ac-Di-Sol™, FMC Biopolymer, Philadelphia, Pa.) were placed in a 30-cc glass bottle. The combined dry components were mixed for 10 min. using a Turbula Shaker Mixer (Willy A. Bachofen AG Maschinenfabrik, Basel, Switzerland). The mixture was then granulated as described in the control above using volatile base solutions for the tests: (a) 2.5 mL of 30% ammonium hydroxide (J. T. Baker Co.), (b) 2.5 mL of 3% ammonium hydroxide, (c) 2.5 mL of 0.00012% ammonium hydroxide, (d) 2.0 mL of 40% tetrabutylammonium hydroxide (Mallinckrodt Co.). The wet granulations were dried overnight at 50° C. for 16 hr. in a forced hot air tray dryer. For each sample, material was analyzed for the level of lactone as described in Example 2, with the modification of using 150 mg of the granulation and the extraction volume of 30 mL. Results are reported in Table 3.

TABLE 3

Unexpected beneficial effect on drug purity for wet granulations of atorvastatin with added volatile bases.

| Example | Volatile Base | % Atorvastatin Lactone (as determined by HPLC) |
| --- | --- | --- |
| 14 | control, no base | 4.35 |
| 15a | 30% ammonium hydroxide | 0.47 |
| 15b | 3% ammonium hydroxide | 0.46 |
| 15c | 0.00012% ammonium hydroxide | 2.75 |
| 15d | 40% tetrabutylammonium hydroxide | below limit of quantification (<0.1%) |

Example 16

Preparation of Wet Granulations of Amorphous Atorvastatin with Drying at Different Temperatures Amorphous atorvastatin calcium as prepared in Example 1 (40.5 mg), 1218.8 mg of microcrystalline cellulose (Avicel PH102™, FMC Biopolymer, Philadelphia, Pa.), 1572.1 mg of lactose, hydrous (Foremost Farms USA, Rothschild, Wis.), 62.5 mg of hydroxypropyl cellulose (Klucel EXF™, Hercules Incorporated, Aqualon Division, Wilmington, Del.), and 93.8 mg of sodium starch glycolate (Explotab™, Penwest Pharmaceuticals Co., Cedar Rapids, Iowa) were placed in a 30-cc glass bottle. The combined dry components were mixed for 10 min. using a Turbula Shaker Mixer (Willy A. Bachofen AG Maschinenfabrik, Basel, Switzerland). The granulating liquid, made in excess, was made by combining 99 g of $H_2O$ with 1 g of polysorbate 80 (TWEEN 80™, Spectrum Chemicals & Lab Products, Gardena, Calif.) in a 125 mL flask and mixing. The powder mixture was then granulated as described in Example 1 using 2.5 mL of the granulating liquid, wet mixing for 4 min. The wet granulation was then divided into three approximately equal portions. Each portion was dried under the following conditions for 16 hr.: (a) 30° C. vacuum oven, (b) 50° C. convection oven, and (c) 70° C. vacuum oven. For each sample, material was analyzed for the level of lactone (based on the ratio of lactone peak integration compared to the total peak integrated areas using HPLC) by adding 300 mg of material to 1:2:2 (v:v:v) of 0.05M ammonium acetate buffer (pH 7.4):acetonitrile:tetrahydrofuran and shaking for 20 minutes. This mixture was filtered using a disposable 0.45 μm polytetrafluoroethylene membrane (Whatman) and analyzed using an HPLC (HP 1100, Zorbax SB-C8 5 μm particle size, 25.0 cm×4.6 mm column, thermostated to 35° C.; injection volume 20 μL; flow rate 1.5 mL/min.; 244 nm detection). The elution used a linear gradient starting from a 67:21:12 (v:v:v) and switching to 54:34:12 (v:v:v) of 0.05M ammonium acetate buffer (pH 5.0):acetonitrile:tetrahydrofuran after 40 minutes (100% of the latter mixture after 55 minutes). Results are reported in Table 4.

TABLE 4

Unexpected beneficial effect on drug purity for wet granulations of atorvastatin when dried at lower temperatures.

| Example | Drying Conditions | % Atorvastatin Lactone (as determined by HPLC) |
|---|---|---|
| 16a | 30° C. vacuum oven | 0.25 |
| 16b | 50° C. convection oven | 1.18 |
| 16c | 70° C. vacuum oven | 4.36 |

What is claimed is:

1. A wet granulated pharmaceutical composition comprising:
   a) from 1 to 40 w/w % of amorphous atorvastatin, or a pharmaceutically acceptable salt thereof,
   b) from 1 to 15 w/w % of a disintegrant selected from the group consisting of sodium starch glycolate, starch, corn starch, pregelatinized starch, sodium alginate, powdered cellulose, hydroxypropylcellulose, magnesium aluminum silicate and polacrilin potassium,
   c) less than 2 w/w % of an alkalinizing agent, in which said alkalizing agent is selected from the group consisting of alkaline earth metal salts, amine polymers and amide polymers, and,
   d) wherein said disintegrant results in an atorvastatin composition which contains less than about 3 w/w % atorvastatin lactone.

2. The wet granulated composition according to claim 1 in which said alkalizing agent is selected from the group consisting of sodium citrate, potassium citrate, sodium carbonate, potassium carbonate, sodium bicarbonate, potassium bicarbonate, sodium phosphate, potassium phosphate, sodium sulfate, potassium sulfate, sodium benzoate, potassium benzoate, sodium ascorbate, potassium ascorbate, calcium carbonate, and magnesium carbonate.

3. The wet granulated pharmaceutical composition of claim 1 in which said disintegrant is present in the quantity of 3 to 8 w/w % of said composition.

4. The wet granulated composition of claim 1 in which said composition is a tablet or capsule.

* * * * *